United States Patent
Han et al.

(10) Patent No.: US 11,112,777 B2
(45) Date of Patent: Sep. 7, 2021

(54) INDEPENDENT HIGH-SPEED SAMPLING FOR AN OIL DRILLING SYSTEM

(71) Applicants: China Petroleum & Chemical Corporation, Beijing (CN); Sinopec Tech Houston, LLC., Houston, TX (US)

(72) Inventors: Jun Han, Houston, TX (US); Sheng Zhan, Houston, TX (US); Fengtao Hu, Houston, TX (US); Jinhai Zhao, Houston, TX (US)

(73) Assignee: CHINA PETROLEUM & CHEMICAL CORPORATION, Beijing (CN)

( * ) Notice: Subject to any disclaimer, the term of this patent is extended or adjusted under 35 U.S.C. 154(b) by 304 days.

(21) Appl. No.: 16/370,389

(22) Filed: Mar. 29, 2019

(65) Prior Publication Data

US 2020/0310389 A1 Oct. 1, 2020

(51) Int. Cl.
*G05B 19/418* (2006.01)
*E21B 47/01* (2012.01)
*G01N 33/28* (2006.01)

(52) U.S. Cl.
CPC .......... *G05B 19/4183* (2013.01); *E21B 47/01* (2013.01); *G01N 33/2823* (2013.01)

(58) Field of Classification Search
CPC ..... G05B 19/4183; E21B 47/01; E21B 47/00; E21B 47/12; E21B 49/00; E21B 47/022; G01N 33/2823; G01V 2200/16; G01V 1/46; G01V 1/22
See application file for complete search history.

(56) References Cited

U.S. PATENT DOCUMENTS

| 2012/0097823 | A1* | 4/2012 | Murray | E21B 47/00 248/550 |
| 2013/0234859 | A1* | 9/2013 | Picioreanu | G01V 11/002 340/853.1 |
| 2017/0159426 | A1* | 6/2017 | Logan | H04B 3/54 |

* cited by examiner

*Primary Examiner* — Melissa J Koval
*Assistant Examiner* — Joseph O Nyamogo
(74) *Attorney, Agent, or Firm* — Novick, Kim & Lee, PLLC; Allen Xue

(57) ABSTRACT

A data sampling and collection system in an oil drilling system includes a data acquirer installed in the measurement sub to transmit a sampling collector identification signal to one of a plurality of sampling collectors coupled to the data acquirer. Each sampling collector includes a sensor and a plurality of random access memory (RAM) pages to store sensor data received from the sensor. When one of the sampling collectors receives the enable signal from the data acquirer, a current RAM page currently receiving sensor data from the sensor continues to receive sensor data without interruption and an immediately preceding RAM page storing a last completed page of received sensor data is transmitted from the one sampling collector to a memory of the data acquirer and from there to a surface computing system. As such, recent data is retrieved and transmitted for processing without interrupting the continuous collection of sensor data.

20 Claims, 9 Drawing Sheets

COLLECTOR ID TABLE

| N-bit collector's ID (Binary) | Sampling Collector ($2^N$ = Total Number of Sampling Collectors) |
|---|---|
| 000 | 1 |
| 001 | 2 |
| 010 | 3 |
| 011 | 4 |
| 100 | 5 |
| 101 | 6 |
| 110 | 7 |
| 111 | 8 |

FIG. 5

INDEPENDENT HIGH-SPEED SAMPLING FOR AN OIL DRILLING SYSTEM

TECHNICAL FIELD

The present disclosure provides an oil drilling system including a drill string and a bottom hole assembly. The bottom hole assembly may include a data acquirer and a plurality of sampling collectors. The sampling collectors may be selected by the data acquirer to provide sensor data to a surface computing system on a surface of the earth.

BACKGROUND

Logging-While-Drilling (LWD) instruments and Measuring-While-Drilling (MWD) instruments are widely used in oil and gas drilling and formation evaluation. For example, these instruments may be installed in a bottom hole assembly (BHA) of a drill string coupled to a derrick above the earth surface.

However, collecting and processing large amounts of sensor data without interruption presents a challenge. For example, in order to obtain data for further processing, one device may be required to request data from another device, obtain permission from the another device to obtain the data, and interrupt the another device from gathering additional data in order for the device to obtain the data.

Accordingly, there is a need for tools and methods for independently and efficiently measuring, processing, and transmitting information at high speeds within the BHA and from the BHA to the surface.

SUMMARY

This disclosure provides a method and apparatus for efficiently acquiring, processing, and transmitting sensor data from sensors of a drill string to a surface computer system for further analysis.

In an aspect of one or more embodiments, there is provided a method for acquiring sensor data for an oil drilling system including a drill string at a wellsite. The method may include (a) transmitting a sampling collector identification signal from a controller to a decoder in a data acquirer installed in the drill string; (b) selecting, by the decoder, a sampling collector from a plurality of sampling collectors based upon the sampling collector identification signal received from the controller; (c) transmitting an enable signal from the decoder to the selected sampling collector which includes a plurality of pages of RAM; (d) determining a current page of RAM which is currently receiving sensor data and an immediately preceding page of RAM which stores a last completed page of received sensor data from among the plurality of pages of RAM of the selected sampling collector; (e) allowing the last completed page of the sensor data from the selected sampling collector to be accessed by the data acquirer; (f) acquiring, by the data acquirer, the last completed page of the sensor data from the selected sampling collector; and (g) storing, by the controller, the last completed page in a memory of the data acquirer In an aspect of one or more embodiments, the method may store in the memory of the data acquirer a predetermined list of sampling collection identification signals.

In an aspect of one or more embodiments, at least one of the sampling collection identification signals appears more than once in the predetermined list.

In an aspect of one or more embodiments, the method may repeat operations (a) through (g) for each sampling collection identification signal in the predetermined list.

In an aspect of one or more embodiments, the drill string includes a bottom hole assembly including a measurement sub and a drill bit.

In an aspect of one or more embodiments, the method may install the data acquirer in the measurement sub of the bottom hole assembly of the drill string.

In an aspect of one or more embodiments, the oil drilling system may further include a first communication device coupled to the drill string and configured to communicate with the data acquirer; a derrick coupled to the drill string and installed above an earth surface including one or more of land and water; a second communication device coupled to the first communication device; and a surface computing system coupled to the second communication device at the wellsite.

In an aspect of one or more embodiments, the method may further include transmitting the last completed page from the memory of the data acquirer to the surface computing system by using the first communication device coupled to the drill string and the second communication device.

In an aspect of one or more embodiments, the first communication device is coupled to the second communication device by a cable.

In an aspect of one or more embodiments, the first communication device is wirelessly coupled to the second communication device.

In an aspect of one or more embodiments, there is provided a data sampling and collection system for oil drilling at a wellsite. The data sampling and collection system may include a drill string including a bottom hole assembly which includes a drill bit and a measurement sub; a data acquirer which is installed in the measurement sub and which includes a controller coupled to a memory and a decoder, wherein the controller transmits a sampling collector identification signal to the decoder, and the decoder transmits an enable signal in response to the sampling collector identification signal; and a plurality of sampling collectors coupled to the data acquirer and each sampling collector including a sensor and a plurality of random access memory (RAM) pages to store sensor data received from the sensor, wherein one of the plurality of sampling collectors receives the enable signal from the decoder so that the decoder selects one of the sampling collectors from the plurality of sampling collectors, wherein the RAM pages include a current RAM page currently receiving sensor data from the sensor and an immediately preceding RAM page storing a last completed page of received sensor data, and wherein the selected sampling collector allows the immediately preceding RAM page storing the last completed page of the received sensor data of the selected sampling collector to be accessed by the data acquirer, and wherein the data acquirer acquires the last completed page of the sensor data from the selected sampling collector and stores the last completed page in the memory of the data acquirer.

In an aspect of one or more embodiments, the memory of the data acquirer stores a predetermined list of sampling collection identification signals.

In an aspect of one or more embodiments, at least one of the sampling collection identification signals appears more than once in the predetermined list.

In an aspect of one or more embodiments, the memory of the data acquirer stores the last completed page of each sampling collector corresponding to the predetermined list of sampling collection identification signals.

In an aspect of one or more embodiments, the data sampling and collection system may further include a derrick coupled to the drill string and installed above an earth surface including one or more of land and water.

In an aspect of one or more embodiments, the data sampling and collection system may further include a first communication device coupled to the drill string and configured to communicate with the data acquirer.

In an aspect of one or more embodiments, the data sampling and collection system may further include a second communication device coupled to the first communication device to receive the last completed page of the sensor data from the first communication device.

In an aspect of one or more embodiments, the data sampling and collection system may further include a surface computing system coupled to the second communication device at the wellsite to receive and store the last completed page of the sensor data.

In an aspect of one or more embodiments, the second communication device is coupled to the first communication device by a cable.

In an aspect of one or more embodiments, the second communication device is wirelessly coupled to the first communication device.

BRIEF DESCRIPTION OF THE DRAWINGS

The teachings of the present invention can be readily understood by considering the following detailed description in conjunction with the accompanying drawings.

FIG. 5 shows a collector identification table according to an embodiment;

DETAILED DESCRIPTION

Figure 1:
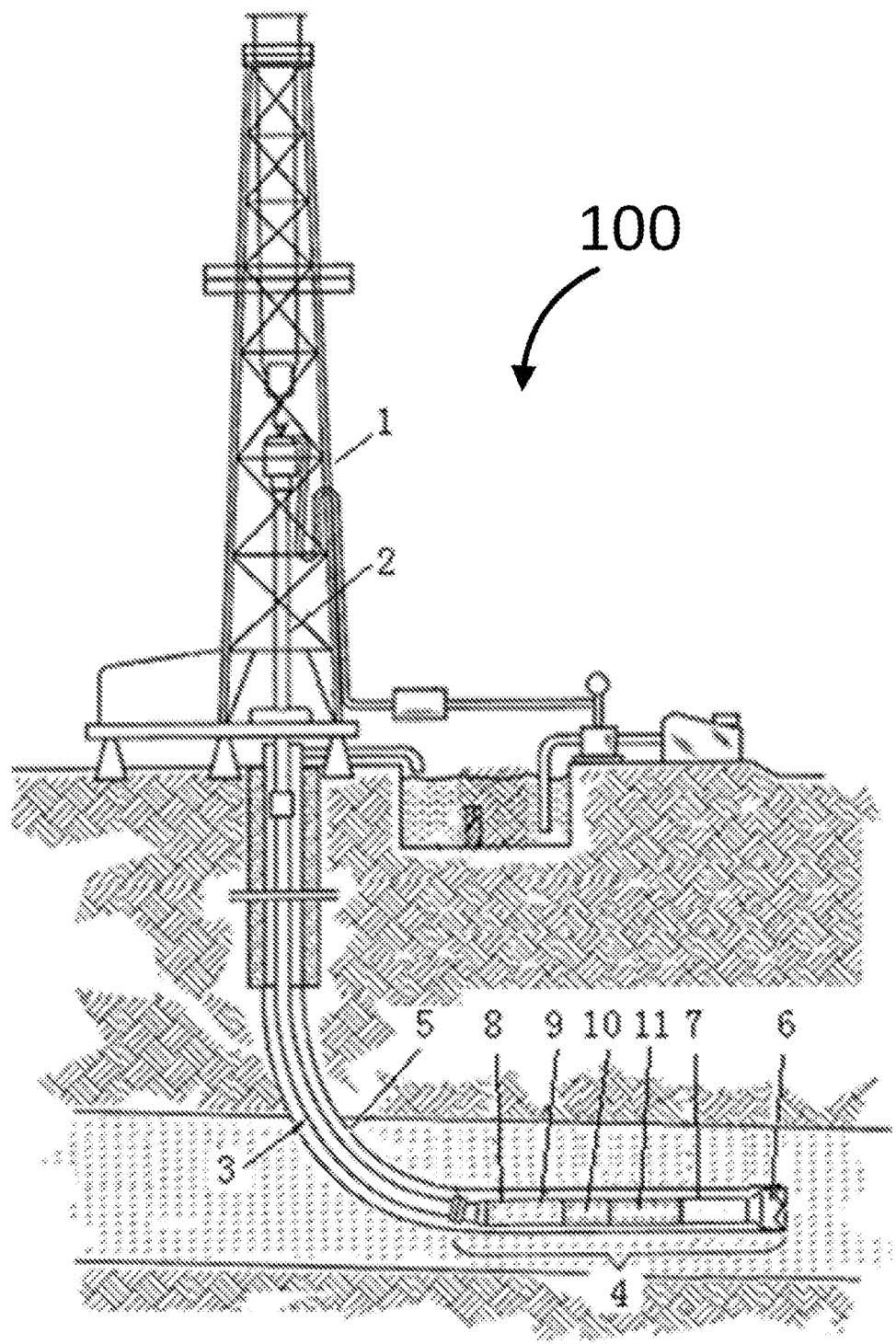
FIG. 1 is a schematic diagram showing an oil drilling system at a wellsite according to an embodiment.

Reference will now be made in detail to embodiments of the present disclosure, examples of which are illustrated in the accompanying drawings. It is noted that wherever practicable, similar or like reference numbers may be used in the drawings and may indicate similar or like elements.

The drawings depict embodiments of the present disclosure for purposes of illustration only. One skilled in the art would readily recognize from the following description that alternative embodiments exist without departing from the general principles of the disclosure.

Oil drilling systems may include logging-while drilling (LWD) instruments or systems which employ formation evaluation tools that measure pressure, gamma ray, resistivity, sonic, porosity and density properties of a formation, in addition to other measurements related to formations. These evaluation tools may include magnetic resonance imaging and formation testing tools which are deployed in a combination string. These formation evaluation tools may also include petrophysical and geosteering capabilities with higher resolution imaging and forward-looking sensors.

Oil drilling systems may also include measuring-while-drilling (MWD) systems, which may for example contain a survey tool that measures formation properties (e.g. resistivity, natural gamma ray, porosity), wellbore geometry (inclination, azimuth), drilling system orientation (tool face), and mechanical properties of the drilling process for drilling a well. MWD instruments or systems measure wellbore trajectory, provide magnetic or gravity tool faces for directional control and a telemetry system that pulses data up through the drill pipe as pressure waves. Examples of MWD measuring systems may use mud pulse or electromagnetic telemetry. MWD technology surveys can be used both as orientation surveys with steerable bottom hole assembly (BHA), or to replace magnetic multi-shot surveys while rotary drilling. Both LWD and MWD systems share this mode of communication to the surface and are combined as one string in a drilling assembly, i.e. a drill string.

FIG. 1 is a schematic diagram showing an oil drilling system at a wellsite according to an embodiment in this disclosure. The drilling system 100 in FIG. 1 has a derrick 1 above the surface, which is shown as land. However, the drilling system 100 may be over any other surface such as water. A kelly 2 drives a drill string 3 into a borehole 5. The lower part of the drill string 3 is a bottom hole assembly (BHA) 4, which includes a non-magnetic drill collar 8 with a MWD system 9 installed therein, LWD instruments 10, a downhole motor 11, the near-bit measurement sub 7, the drill bit 6, etc. During the drilling operation, the drilling system 100 may operate in the rotary mode, in which the drill string 3 is rotated from the surface either by the rotary table or a motor in the traveling block (i.e., a top drive). The drilling system 100 may also operate in a sliding mode, in which the drill string 3 is not rotated from the surface but is driven by the downhole motor 11 rotating the bit downhole. Drilling mud is pumped from the surface through the drill string 3 to the drill bit 6, being injected into the annulus between the drill string 3 and the wall of the well. The drilling mud carries the cuttings up from the well to the surface.

The non-magnetic drill collar 8 has the MWD system 9, which includes a package of instruments for measuring inclination, azimuth, well trajectory, etc. Also included in the non-magnetic drill collar 8 or other locations in the drill string 3 are LWD instruments 10 such as a neutron-porosity measurement tool and a density measurement tool, which are used to determined formation properties such as porosity and density. The instruments may be electrically or wirelessly coupled together, powered by a battery pack or a power generator driven by the drilling mud. All information gathered may be transmitted to the surface via a mud pulse telemetry system, electromagnetic transmission, or other communication system.

The measurement sub 7 may be disposed between the downhole motor 11 and drill bit 6, measuring formation resistivity, gamma ray, and the well trajectory. The data may be transmitted through the cable embedded in the downhole motor 11 to MWD or other communication devices. The downhole motor 11 may be connected to a bent housing that is adjustable at the surface from 1° to 3°, preferably up to 4°. Due to the slight bend in the bent housing, the drill bit 6 can drill a curved trajectory.

Figure 2:
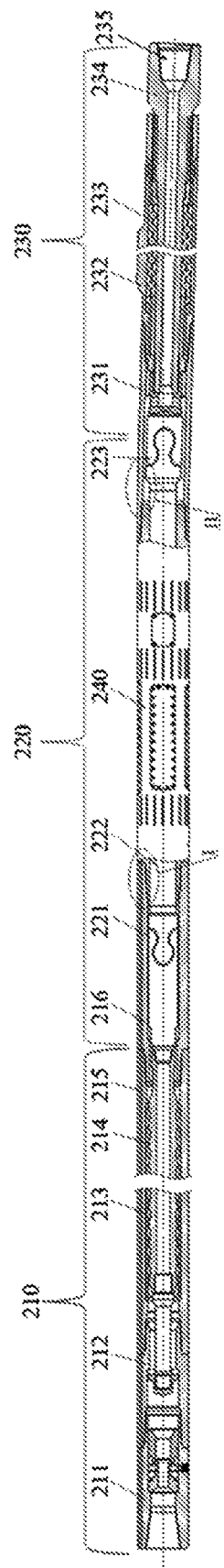
FIG. 2 is a schematic diagram showing a drilling tool according to an embodiment.

FIG. 2 is a schematic diagram showing an example of a BHA 4 of a drill string 3 according to an embodiment. The BHA includes a downhole motor 210 (which is an example of downhole motor 11 in FIG. 1), a universal joint (i.e., u-joint) assembly 220, a measurement sub 240 (which is example of measurement sub 7 in FIG. 1) that fits over the u-joint connecting rod 222, and a drive shaft assembly 230. The universal joint assembly 220 contains an upper u-joint 221 proximal to the downhole motor 210, a lower u-joint 223 distal from the downhole motor 210, and the u-joint connecting rod 222 connecting the upper and lower u-joints. The drive shaft assembly 230 has a tubular drive shaft 234 having a proximal end coupled to the bent housing 231 and a distal end which is a box end 235 adapted to hold the drill bit (not shown in FIG. 2). A thrust bearing 233 is disposed between the drive shaft 234 and the bearing housing 232.

The drilling mud is pumped through the downhole motor 210, generating rotational movement of the rotor 214, which is translated through the u-joint assembly 220 to the drive shaft assembly 230. The drill bit (not shown in FIG. 2) installed in the box end 235 in the shaft assembly 230 is driven to rotate accordingly. The shaft assembly 230 also bears the axial and radial thrusts generated by drilling. The measurement sub 240 fits over the u-joint connecting rod 222 like a sleeve. The measurement sub 240 rotates together with the drilling assembly and, at the same time, measures formation information and wellbore trajectory, etc.

The downhole motor 210 can be a positive displacement motor (PDM), a Moineau motor, a turbine, or other suitable motors known in the art. As shown in FIG. 2, the downhole motor 210 has a dump valve assembly 211 and an anti-drop assembly 212. The dump valve assembly 211 has an open position or a closed position. When the downhole motor 210 is being tripped up, a bypass valve is open so that the mud can be drained into the annulus in the borehole. Furthermore, when the drilling mud flow rate and pressure reach certain pre-determined values, the bypass valve closes so that the drilling mud flows through the downhole motor 210. The anti-drop assembly 212 is also called safety-catch assembly, which can be used to remove the downhole motor 210 from the well when there is a motor connection failure. The anti-drop assembly 212 may cause the mud pressure to quickly rise, alerting the surface about the connection failure when it occurs.

As shown in FIG. 2, the measurement sub 240 is disposed about the u-joint connecting rod 222 between the upper u-joint 221 and the lower u-joint 223. In this embodiment, the measurement sub 240 is tubular in shape with a hollow center in its longitudinal direction. The u-joint connecting rod 222 extends through the hollow center of the measurement sub 240. The upper u-joint 221 (on the proximal end of the u-joint connecting rod 222) is coupled to the distal end of the rotor 214 while the lower u-joint 223 (on the distal end of the u-joint connecting rod 222) is coupled to the proximal end of the drive shaft 234. The stator adaptor 216 serves as a transition piece to couple together the measurement sub 240 and the downhole motor 210. The upper proximal end of the stator adaptor 216 is coupled to the stator 213 of the downhole motor 210 while its distal end is connected to the upper threadable connection of the measurement sub 240. The lower threadable connection of the measurement sub 240 is connected to the bent housing 231. The length of the measurement sub 240 may vary according to instruments it accommodates. The length of the u-joint connecting rod 222 and the length of the stator adaptor 216 vary according to the length of the measurement sub 240, and vice versa.

Data gathered by the measurement sub 240 are sent to the MWD tools located above the downhole motor 210 and transmitted to the surface from there. The measurement sub integrates modules for detecting gamma ray, resistivity, and formation density. The measurements are directional or azimuthal so that data better reflects properties of formation near the borehole sections by sections. Since the azimuthal measurement of the borehole is usually obtained using fluxgate magnetometers, the measurement is subject to interference from the electromagnetic field surrounding the tool.

As discussed above, the measurement sub 240 may contain sensors and circuitries for measuring resistivity, gamma ray, and wellbore trajectory such as wellbore inclination. In addition, the measurement sub 240 can be powered by a battery pack installed in the measurement sub 240 itself or at a location above the downhole motor 210, or by power generated in a turbine generator driven by the drilling mud. Accordingly, there are channels for data communications and/or power transmission between the measurement sub 240 and instruments above the downhole motor 210.

In an embodiment shown in FIG. 2, the power for the measurement sub 240 may be supplied by instruments above the downhole motor 210. The stator 213 in the downhole motor has one or more conduits 215 for housing electrical wires/data cables, connecting the measurement sub 240 and instruments (MWD tools, not shown) above the downhole motor 210. The conduit 215 can be a channel machined into the surface of the stator 213 or built in the elastomer layer inside the stator 213. The data cable allows stable and fast data transmissions.

In an embodiment, the measurement sub 240 may also have a wireless communication module, which communicates with a corresponding module installed above the downhole motor 210, establishing data communications between the two modules by electromagnetic signals.

Figure 3:
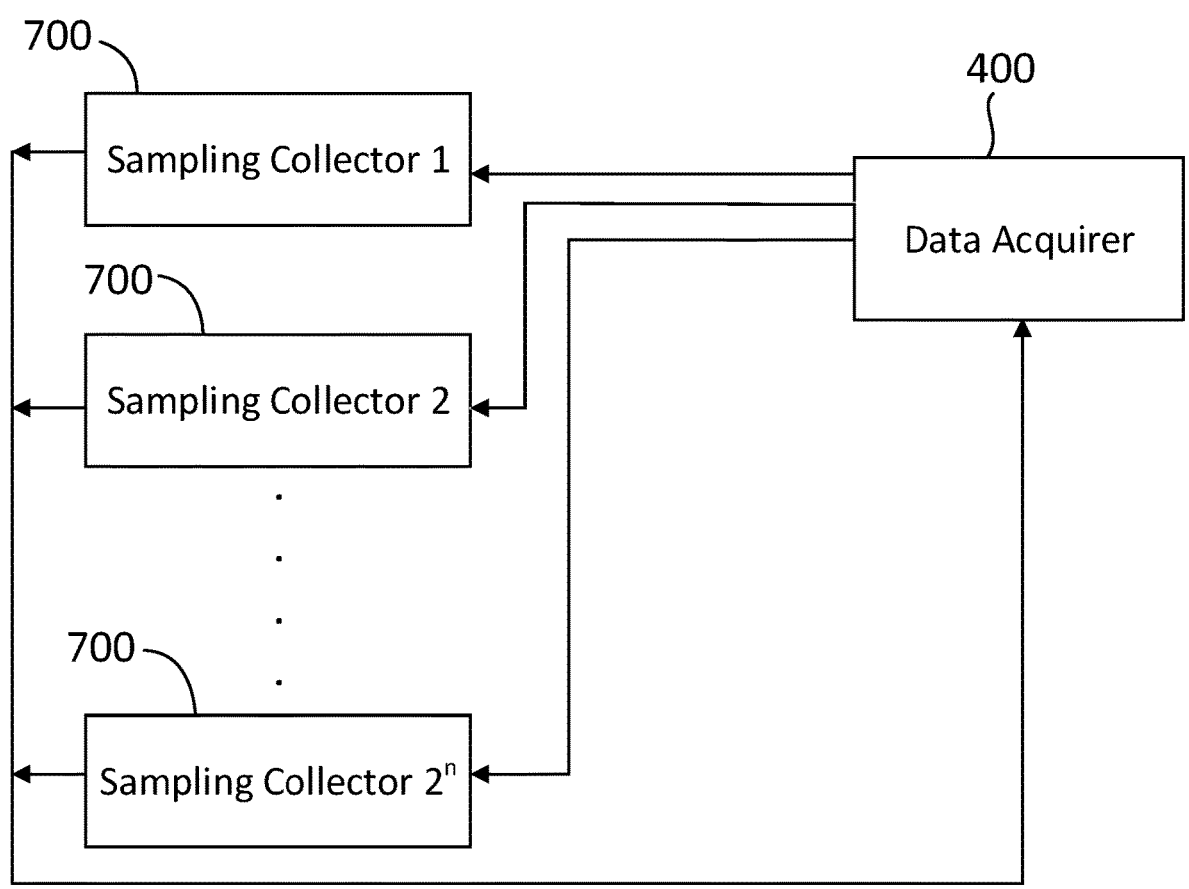
FIG. 3 is a schematic diagram showing a data acquirer and a plurality of sampling collectors according to an embodiment.

As discussed above, the measurement sub 240 is an example of measurement sub 7 in a bottom hole assembly 4 of drill string 3 in FIG. 1. FIG. 3 is a schematic diagram showing a data acquirer 400 and a plurality of sampling collectors 700 according to an embodiment, which may be installed in bottom hole assembly 4 of FIG. 1. The data acquirer 400 may acquire data from any sampling collector 700 which may be collecting sensor data related to MWD instruments or systems, LWD instruments or systems, or other instruments or systems for the oil drilling system. The data acquirer 400 may be installed in the measurement sub 7 or another location of the bottom hole assembly 4. One or more sampling collectors 700 may be installed within or coupled to the measurement sub 7. One or more sampling collectors 700 may be installed within or coupled to other locations of the bottom hole assembly (BHA) 4.

Figure 4:
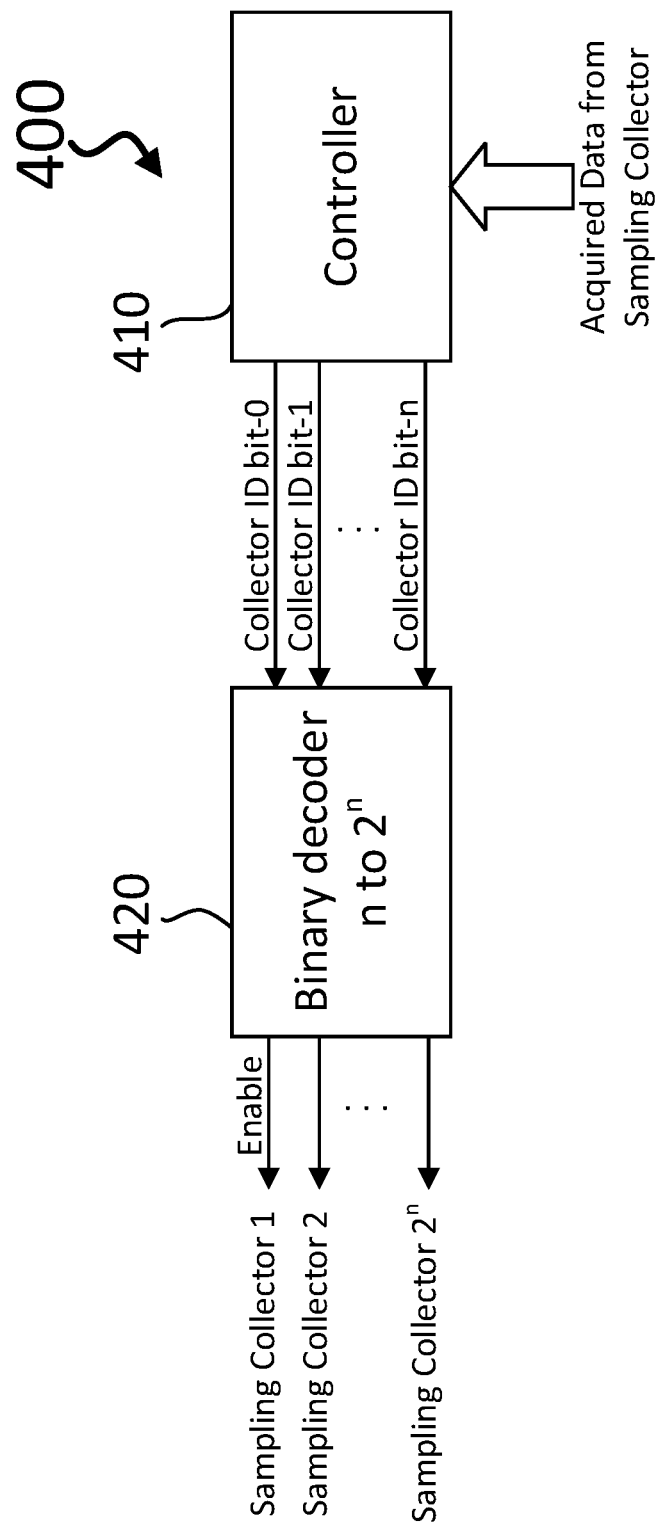
FIG. 4 is a schematic diagram showing an embodiment of a data acquirer of FIG. 3.

FIG. 4 is a schematic diagram showing an embodiment of a data acquirer 400 of FIG. 3. The data acquirer 400 may include a controller 410. Examples of a controller 410 include a microprocessor and a field programmable gate array (FPGA). However, any electronics forming a controller may be used as controller 410. The controller 410 may include an internal memory or may be coupled to a separate memory (not shown). Controller 410 is configured to acquire sensor data from one or more sampling collectors 700. The sensor data may also be referred to as acquired data as shown in FIG. 4. The controller 410 also stores instructions which may be one or more computer programs. This set of instructions may cause the controller 410 to send sampling collector identification signals to a binary decoder 420, which is coupled to controller 410 in the data acquirer 400. The controller 410 may also receive instructions from a separate memory (not shown). Alternatively, controller 410 may receive instructions from a mud pulse.

In the example shown in FIG. 4, the number of sampling collector identification signals is $2^N$, which may correspond to the number of sampling collectors. For example, in an embodiment shown in the Collector ID table in FIG. 5, N is equal to 3 and the number of sampling collector identification signals (N-bit collector's ID) equals the number of sampling collectors. In the embodiment shown in FIG. 5, there are eight sampling collectors with each sampling collector having a corresponding sampling collector identification signal (N-bit collector ID). For example, N-bit collector ID "011" is a sampling collector identification signal which identifies sampling collector number 4. The value of N may be less than or greater than 3 depending on the number of sampling collectors 700 which may be configured to allow sensor data to be acquired by the data acquirer 400 by reading sensor data from a memory of the sampling collector. For example, if there are more than eight sampling collectors, N will have a greater value than 3 in order to provide additional sampling collection identification signals.

As discussed above, the controller 410 stores instructions which may be one or more computer programs. This set of instructions may cause the controller 410 to send sampling collector identification signals to a binary decoder 420, which is coupled to controller 410 in the data acquirer 400. The sampling collector identification signals may be sent in any order set forth by the set of instructions. For example, it may be desirable to obtain (acquire) sensor data more frequently from one sampling collector than another sampling collector. Therefore, a request for sensor data from one sampling collector may be made more frequently than a request for sensor data from another sampling collector. Accordingly, the frequency of the requests from each sampling collector may vary.

In one example, the data acquirer 400 may wish to repeatedly obtain sensor data from sampling collectors (SCs) in the following order: SC4, SC5, SC8, SC4, SC7, SC 6, SC4, SC1, SC2, SC3, and SC4, and therefore will send an N-bit collector ID (sampling collector identification signal) to decoder 420 in the following order: 011, 100, 111, 011, 110, 101, 011, 000, 001, 010, and 011. After each sampling collector identification signal is received by decoder 420, the decoder 420 may send an enable signal (a high signal) to the corresponding sampling collector 700, which is identified by the sampling collector identification signal. Although this is one example, sensor data from the sampling collectors 700 may be requested in any order and with as much frequency as desired in accordance with the set of instructions executed by controller 410. Accordingly, the data acquirer 400 may continuously acquire the desired sensor data from the sampling collectors 700, which can then be communicated to a surface computing system (not shown) through a cable, wirelessly, mud pulses, or in any other suitable manner.

Figure 6:
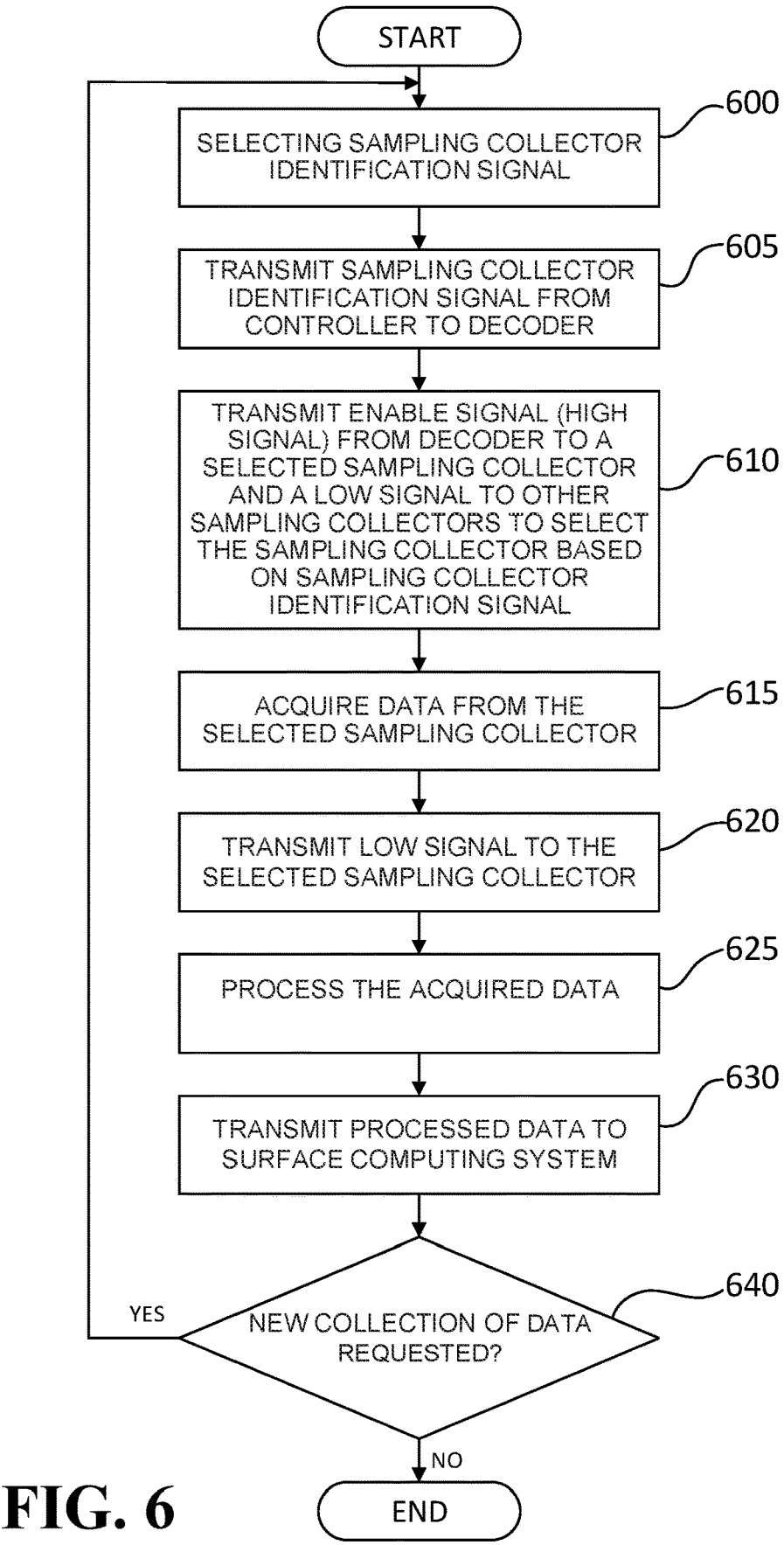
FIG. 6 is a flow chart showing a process of acquiring data for a data acquirer according to an embodiment.

FIG. 6 is a flow chart showing a process of acquiring data for a data acquirer according to an embodiment. In this example, a sampling collector identification signal is selected by the controller 410 (operation 600) to select a sampling collector and is transmitted from controller 410 to decoder 420 (operation 605). The decoder 420 transmits an enable signal (high signal or selection signal) from decoder 420 to select the selected sampling collector 700 based on the sampling collector identification signal and the decoder 420 transmits a disable signal (low signal) to other unselected sampling collectors 700 (operation 610). Alternatively, the decoder 420 maintains a low signal at the other unselected sampling collectors 700 by not sending a high signal to the other unselected sampling collectors 700.

After the sampling collector 700 is selected by transmitting the enable signal, the data acquirer 400 acquires sensor data from the selected sampling collector 700 (operation 615). The selected sampling collector 700 may process data sensed or collected from one or more sensors of the selected sampling collector 700 to provide sensor data in a form that can be acquired by the data acquirer 400. The data acquirer 400 may further process the sensor data to prepare the sensor data for transmission to the surface computing system (not shown). Regardless of the amount of processing by any sampling collector 700 or data acquirer 400, the data to be collected by any sampling collector and acquired by the data acquirer 400 is based upon data sensed or collected from sensors and is referred to as sensor data.

After the data acquirer 400 acquires the sensor data from the selected sampling collector 700, the data acquirer 400 may deselect the selected sampling collector 700 by transmitting a disable signal (low signal or deselection signal) to the previously selected sampling collector 700 (operation 620). Viewed in another way, the decoder 420 may have transmitted an enable signal with a rising edge to the selected sampling collector 700 to select the sampling collector for a period of time and with a falling edge to deselect the sampling collector 700. Regardless of the viewpoint, the sampling collector 700 detects whether a received signal is high or low and the sampling collector 700 allows data to be acquired by the data acquirer 400 when the signal is high and does not allow data to be acquired by the data acquirer when the signal is low. The data acquirer 400 may process the sensor data (acquired data) (operation 625) acquired while the selected sampling collector 700 is receiving a high signal and may transmit the sensor data (which has been processed) to a surface computing system (operation 630). The sensor data may or may not require processing before transmitting the sensor data to the surface computing system. However, once the sensor data has been sent to the surface computing system, the data acquirer 400 may request sensor data from a sampling collector 700 based on the next sampling collection identification signal (operation 640) until there are no additional requests for sensor data (operation 640).

Although FIG. 6 shows a flow chart showing a process of acquiring data for a data acquirer 400 according to an embodiment, this embodiment is an example. In another example, data acquirer 400 may store sensor data from more than one sampling collectors 700 and then transmit this stored sensor data to the surface computing system.

Figure 7:
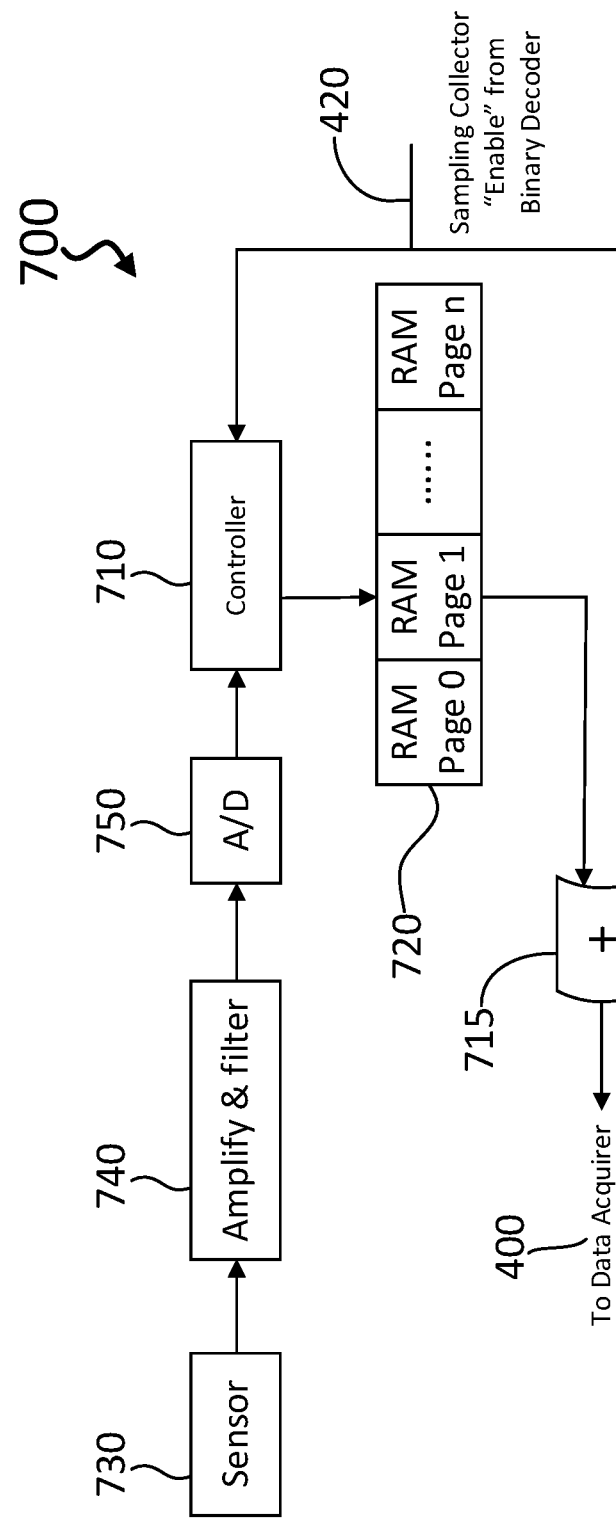
FIG. 7 is a schematic diagram showing an embodiment of a sampling collector of FIG. 3.

FIG. 7 is a schematic diagram showing an embodiment of a sampling collector 700 of FIG. 3. As shown in FIG. 7, a sampling collector 700 is configured to receive an enable signal (high signal) or a low signal from a decoder 420 in data acquirer 400 of FIG. 4 to select or deselect sampling collector 700. If sampling collector 700 in FIG. 7 receives an enable signal (high signal), the sampling collector 700 is selected by the data acquirer 400 to transmit sensor data to the data acquirer 400. For example, the selected sampling collector 700 may include a controller 710 and a logic gate 15, which are configured to receive the enable signal from the data acquirer 400. Examples of the logic gate 715 may be an AND gate or a NAND (NOT AND) gate. The logic gate 715 may be configured to transmit sensor data upon receiving an enable signal (high signal) from the data acquirer 400 in FIG. 4.

Examples of a controller 710 include a microprocessor and a field programmable gate array (FPGA). However, any electronics forming a controller may be used as controller 710. The controller 710 may include an internal memory or may be coupled to a separate memory (not shown), which may include a first predetermined memory location and a second predetermined memory location. The first predetermined memory location and the second predetermined memory location may store for example a zero (low signal) or a one (high signal). The first predetermined memory location may indicate whether the sampling collector 700 has currently detected receipt of a low signal or high signal and the second predetermined memory location may indicate the immediately preceding detection of a low signal or a high signal.

In one example, both the first predetermined memory location and the second predetermined memory location may store a zero (low signal) because an enable signal has not yet been received. Once an enable signal (high signal) is received by a sampling collector 700, the sampling collector 700 may store a one in the first predetermined memory location. If the sampling collector 700 subsequently determines that the enable signal (high signal) is still being received, the sampling collector 700 may store a one in both the first predetermined location and the second predetermined location to reflect the enable signal has not changed. If the sampling collector 700 receives a low signal, then the sampling collector 700 may store a zero in the first predetermined location to indicate that the sampling collector 700 is no longer receiving an enable signal. Instead, the sampling collector 700 is currently receiving a disable signal (low signal). If the sampling collector 700 subsequently determines that the disable signal (low signal) is still being received, the sampling collector 700 may store a zero in both the first predetermined location and the second predetermined location to reflect that the disable signal has not changed. By referring to the first predetermined memory location and the second predetermined memory location, the controller 710 of the sampling collector 700 can determine whether to allow (permit) the data acquirer 400 to acquire (read) sensor data from a random access memory (RAM) 720 shown in FIG. 7.

As shown in FIG. 7, the controller 710 may be coupled to random access memory (RAM) 720 divided into pages of RAM. The number of pages of RAM is n where n is a whole number greater than or equal to the number 2. In FIG. 7, RAM Page zero (RAM Page 0) corresponds to the page of RAM currently receiving sensor data. RAM Page zero has not yet been completely filled with sensor data. RAM page zero may be partially filled with sensor data. RAM Page one (RAM Page 1) corresponds to the last completed page filled with sensor data before the current page (RAM Page 0) began being filled with sensor data. In FIG. 7, RAM Page 1 is the page of RAM containing sensor data which immediately precedes the sensor data stored in the RAM page currently being filled with the most recent sensor data, which is RAM page 0. RAM Pages 2 through N are previous RAM pages completely filled with sensor data.

As shown in FIG. 7, sensor 730 senses data, which is amplified and filtered by an electrical circuit (electrical circuitry) 740 and converted through an analog to digital converter 750 to sensor data. The electrical circuit 740 may include one or more operational amplifiers and associated circuitry. The electrical circuit 740 may be an application specific integrated circuit or other hardware device. The sensor data is transmitted from the analog to digital converter 750 to the controller 710, which transmits the sensor data to the current page of RAM 720 (unfilled page of RAM which is currently being filled). In FIG. 7, RAM Page 0 is currently being filled. As indicated in FIG. 7, filling pages of RAM in RAM 720 with sensor data is independent of the enable signal (high signal) or the low signal from the data acquirer 400. The enable signal (high signal) or a low signal does not interrupt the continuous sensor data collection operation performed by sampling collector 700. Instead, when sampling collector 700 receives an enable signal from data acquirer 400, the enable signal is received by controller 710 and logic gate 15 so that the last completed filled RAM page of sensor data (RAM Page 1) may be acquired (read) by the data acquirer 400 from the RAM 720 without interrupting the filling of the current page of RAM receiving sensor data (RAM Page 0).

Figure 8:
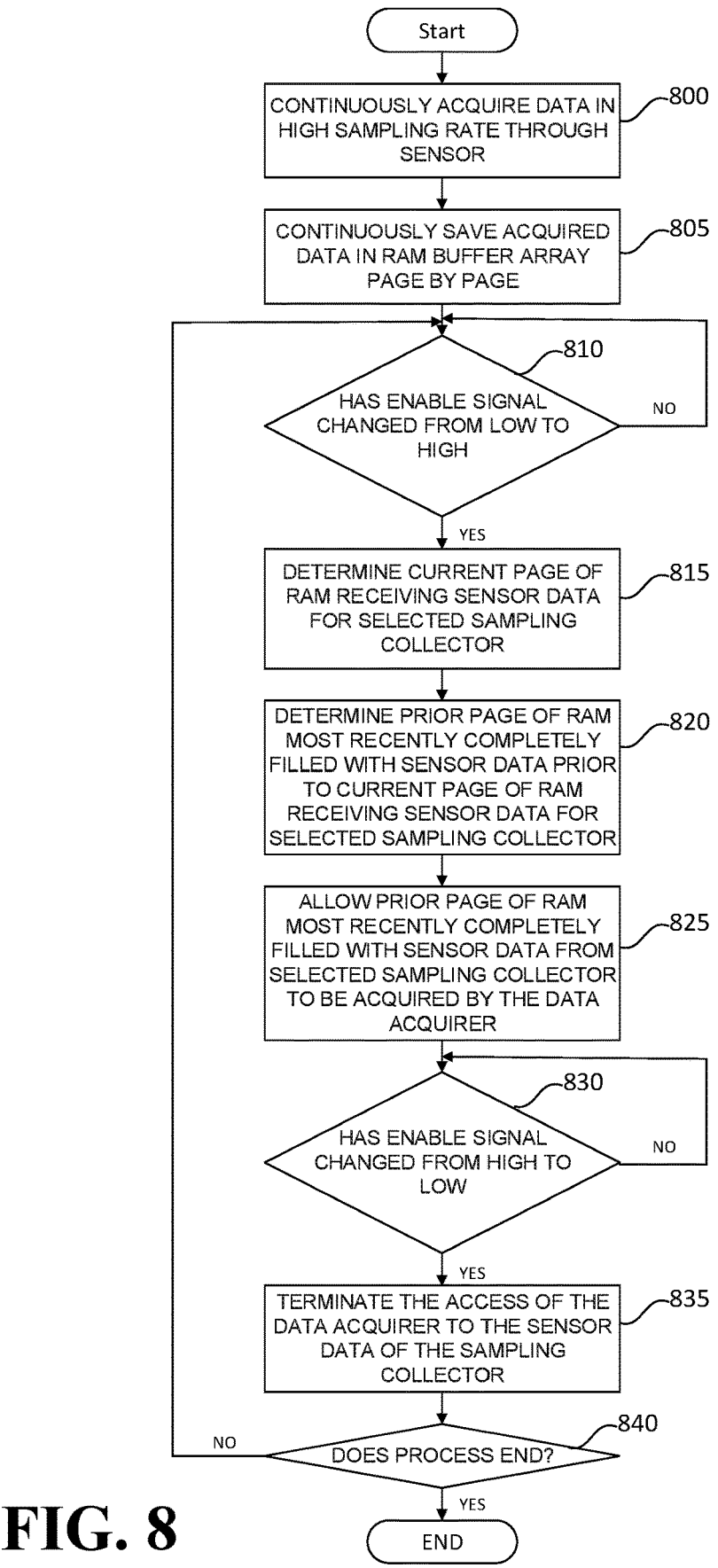
FIG. 8 is a flow chart showing a process of collecting data for a sampling collector according to an embodiment.

FIG. 8 is a flow chart showing a process of collecting data for a sampling collector according to an embodiment. In this example, a sampling collector 700 continuously acquires data with a high sampling rate through a sensor 730 (operation 800). This acquired data may be continuously amplified, filtered and converted by electrical circuit 740 and analog to digital converter 750 to provide data which can be stored in RAM 720. This data (sensor data) is stored in RAM 720 under the control of controller 710 (operation 805). The continuous acquisition and storage of data refers to continuously acquiring and storing data regardless of the selection or deselection of the sampling collector 700. As discussed above, by referring to the first predetermined memory location and the second predetermined memory location, the controller 710 of the sampling collector 700 can determine whether to allow (permit) the data acquirer 400 to acquire (read) sensor data from a random access memory (RAM) 720 shown in FIG. 7. However, the acquisition and storage of data remains continuous even when other operations are performed in FIG. 8.

For example, the controller 710 refers to the first predetermined memory location and the second predetermined memory location to determine a selection/deselection cycle of sampling collector 700. As discussed above, the first predetermined memory location may indicate whether the sampling collector 700 has currently detected receipt of a low signal or high signal and the second predetermined memory location may indicate the immediately preceding detection of a low signal or a high signal. If the signal is detected to be low and a zero is stored in the first predetermined memory location as well as the immediately preceding detected signal being low and stored as a zero in the second predetermined memory location, the sampling collector 700 continues to fill the current RAM page with sensor data (operation 810), and does not allow data acquirer 400 to acquire (read or obtain) data from the sampling collector 700.

If the signal changes from low to high because sampling 700 has been selected (operation 810), the sampling collector 700 stores one in the first predetermined memory location to indicated detection of an enable signal, and the current page of RAM receiving sensor data in the RAM 720 is determined (identified) (operation 815) and the prior page of RAM most recently completely filled with sensor data prior to the current page of RAM receiving sensor data is determined (operation 820). The prior page of RAM, which has been most recently completely filled with sensor data prior to the current page of RAM currently receiving sensor data from a sensor, can be acquired by the data acquirer 400 from the sampling collector 700 (operation 825). In this example, the sampling collector 700 continuously and periodically detects whether the signal is high or low in order to detect changes in state (one to zero or zero to one) of the signal from the data acquirer 400.

In this example, if the sampling collector 700 has stored a one in the first predetermined memory location due to the detection of a high signal and a zero in the second predetermined memory location, then the sampling collector 700 will again detect whether the signal is high or low. If the sampling collector 700 detects a high signal, then the sampling collector 700 stores a one in the first predetermined memory to reflect the current state of the signal and a one in the second predetermined memory location to reflect the immediately preceding detection. This indicates that the signal is still high and the sampling collector 700 is still receiving an enable signal. As long as the current state of the signal remains high (sampling collector 700 is receiving an enable signal) as indicated in the first predetermined memory location, the controller 710 of the sampling collector 700 will allow the data acquirer 400 to acquire the most recently completely filled page of RAM. However, if the enable signal changes from high to low in operation 830, then the controller 710 will store a zero in the first predetermined memory location. The sampling collector 700 may terminate the access of the data acquirer 400 to the sensor data of the sampling collector 700 (operation 835). If the operations are not concluded, then the process returns to operation 810 (operation 840). Because the signal from the data acquirer 400 is constantly monitored by sampling collector 700, the sampling detector may detect an immediately subsequent low signal and store a zero in both the first predetermined memory location and the second predetermined memory location, or may detect a high signal and store a one in the first predetermined memory location and a zero in the second predetermined memory location (operation 810). As discussed above, there is no interruption of the collection of data by the sampling collector, because these operations are performed very quickly.

Figure 9:
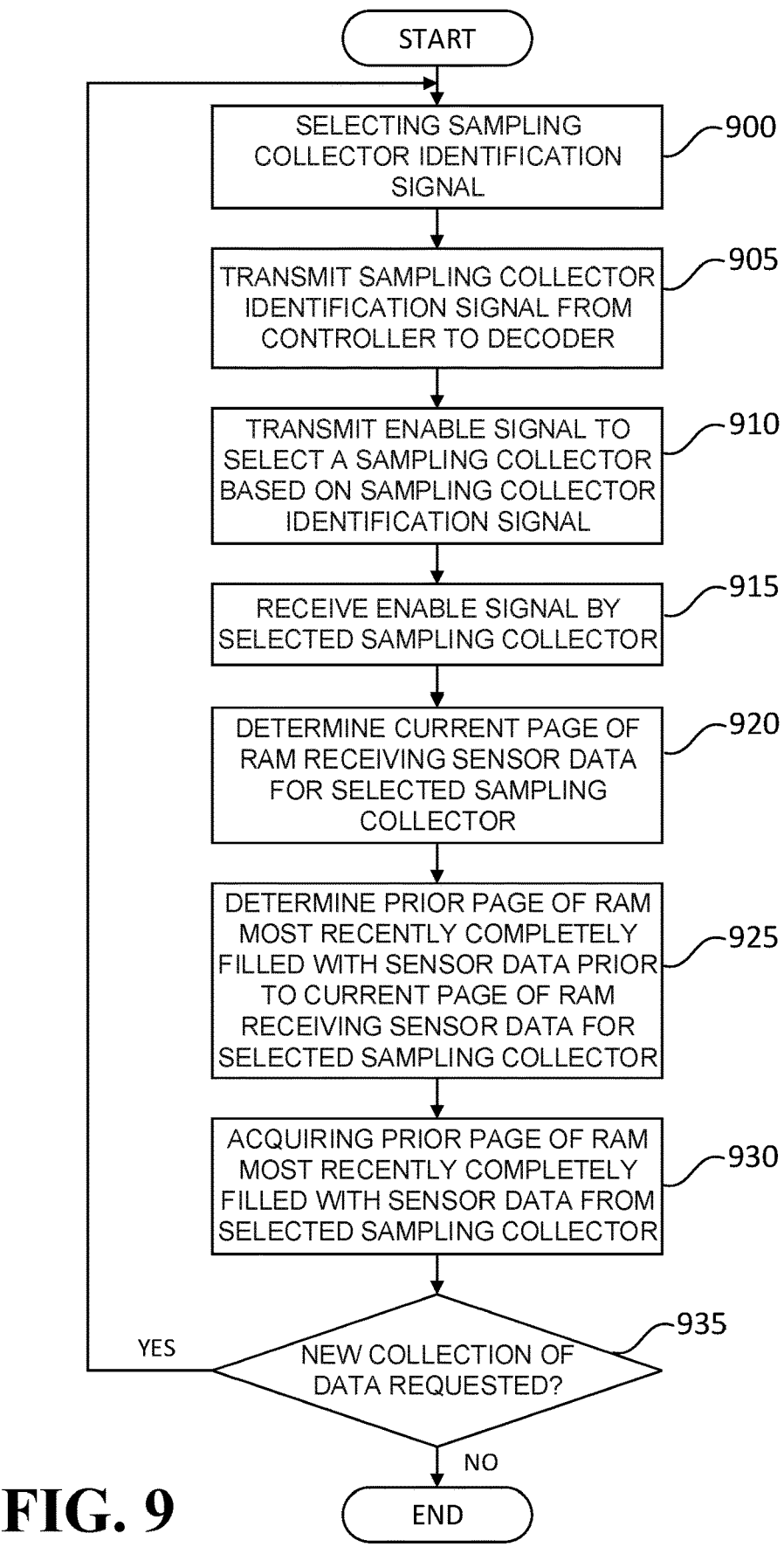
FIG. 9 is a flow chart for showing a process for acquiring sensor data for an oil drilling system according to an embodiment.

FIG. 9 is a flow chart for showing a process for acquiring sensor data for an oil drilling system according to an embodiment. The oil drilling system may include a drill string at a wellsite as shown in FIG. 2. FIG. 9 provides a flow chart showing an overall process flow of both the data acquirer 400 and sampling collector 700 of and embodiment in FIG. 3. Examples of the data acquirer 400 and sampling collector 700 are shown in FIG. 4 and FIG. 7.

Referring to FIG. 9, a controller 410 of a data acquirer 400 may select a sampling collector identification signal corresponding to one of a plurality of sampling collectors 700 according to set of instructions stored in the controller 410 or a memory coupled to controller 410 (operation 900). Alternatively, controller 410 may receive instructions from mud pulse signals transmitted from the surface by modulating the mud flow using a mud pulser above the BHA. Such mud pulse signals may also be generated by turning on or off the mud pump on the surface. The set of instructions may include referencing a table of predetermined sampling collector identification signals, which are stored in a particular order based on how frequently each sampling collector is to be selected to obtain sensor data. The sampling collector identification signal may be transmitted to a decoder 420 in the data acquirer 400 (operation 905). Based on the sampling collector identification signal, the decoder 420 may transmit an enable signal to select a sampling collector (operation 910). The selected sampling collector 700 may include a plurality of pages of RAM of a RAM 720.

After the enable signal is received by the selected sampling collector (operation 915), a controller 710 may determine the current page of RAM receiving sensor data (operation 920) and determine the prior page of RAM most recently filled with sensor data prior to the current page of RAM, which continues to receive sensor data without interruption (operation 925). The prior page of RAM may also be referred to as an immediately preceding page of RAM which stores a last completed page of received sensor data from among the plurality of page of RAM of RAM 720 in the selected sampling collector 700.

Because both the controller 710 and the logic gate 715 have both received the enable signal, the controller 710 can permit the data acquirer 400 to have access to the prior page of RAM most recently filled with sensor data prior to the current page of RAM from the selected sampling collector 700, so that the data acquirer 400 can acquire the prior page of RAM most recently filled with sensor data prior to the current page of RAM from the selected sampling collector 700 (operation 930). As indicated in FIG. 9, once the acquisition is completed in operation 930, a new collection of data may be requested in operation 935, and a next sampling collector 700 may be selected from among the plurality of sampling collectors 700 in operation 900. The next sampling collector 700 may be the same as the last sampling collector 700, which permits the data acquirer 400 to acquire sensor data, or another sampling collector 700 may be selected in operation 900 in accordance with the set of instructions stored in controller 410 or a memory coupled to controller 410.

Processes, functions, methods, and/or software in apparatuses described herein may be recorded, stored, or fixed in one or more non-transitory computer-readable media (computer readable storage (recording) media) that includes program instructions (computer readable instructions) to be implemented by a computer to cause one or more processors to execute (perform or implement) the program instructions. The media may also include, alone or in combination with the program instructions, data files, data structures, and the like. The media and program instructions may be those specially designed and constructed, or they may be of the kind well-known and available to those having skill in the computer software arts. Examples of non-transitory computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions may be executed by one or more processors. The described hardware devices may be configured to act as one or more software modules that are recorded, stored, or fixed in one or more non-transitory computer-readable media, in order to perform the operations and methods described above, or vice versa. In addition, a non-transitory computer-readable medium may be distributed among computer systems connected through a network and program instructions may be stored and executed in a decentralized manner. In addition, the computer-readable media may also be embodied in at least one application specific integrated circuit (ASIC) or Field Programmable Gate Array (FPGA).

While embodiments of this disclosure have been shown and described, modifications can be made by one skilled in the art without departing from the spirit or teaching of this invention. The embodiments described herein are exemplary only and are not limiting. Many variations and modifications of methods, systems and apparatuses are possible and are within the scope of the invention. Accordingly, the scope of protection is not limited to the embodiments described herein, but is only limited by the claims. The scope of the claims shall include all equivalents of the subject matter of the claims.

What is claimed is:

1. A method for acquiring a plurality of sensor data for an oil drilling system including a drill string at a wellsite, wherein the drill string has a data acquirer and a plurality of sampling collectors coupled to the data acquirer, wherein each of the plurality of sampling collectors has a sensor and a plurality of pages of random access memory (RAM) to store sensor data received from the sensor, wherein the data acquirer has a decoder and a memory, and, during operation, the data acquirer asynchronously acquires the plurality of sensor data individually from one of the plurality of sampling collectors, the method comprising:
   (a) acquiring a plurality of sensor data by of each of said sensors respectively contained in the plurality of sampling collectors independently, and storing the currently acquired sensor data in the plurality of pages of RAM in each of the plurality of sampling collectors;
   (b) transmitting a sampling collector identification signal from a controller to a decoder to the selected sampling collector;
   (c) selecting, by the decoder, a sampling collector from a plurality of sampling collectors based upon the sampling collector identification signal received from the controller;
   (d) transmitting an enable signal from the decoder to the selected sampling collector;
   (e) determining, among the plurality of pages of RAM in the selected sampling collector, a current page of RAM that is currently receiving the plurality of sensor data and an immediately preceding page of RAM that stores a last completed page of received plurality of sensor data from among the plurality of pages of RAM of the selected sampling collector;
   (f) allowing the last completed page of the plurality of sensor data from the selected sampling collector to be accessed by the data acquirer and disallowing the current page of RAM of the acquired plurality of sensor data from the selected sampling collector to be accessed by the data acquirer;
   (g) acquiring, by the data acquirer, the last completed page of the plurality of sensor data from the selected sampling collector without interrupting filling the current page of RAM with the plurality of sensor data, and without interrupting operation of a plurality of sampling collectors that are not selected; and
   (h) storing, by the controller, the plurality of sensor data in the last completed page of RAM in a memory of the data acquirer.

2. The method of claim 1, further comprising storing in the memory of the data acquirer a predetermined list of sampling collection identification signals.

3. The method of claim 1, wherein at least one of the sampling collection identification signals appears more than once in the predetermined list.

4. The method of claim 1, further comprising repeating operations steps (a) through (h) for each sampling collection identification signal in the predetermined list.

5. The method of claim 1, wherein the drill string includes a bottom hole assembly including a measurement sub and a drill bit.

6. The method of claim 5, further comprising installing the data acquirer in the measurement sub of the bottom hole assembly of the drill string.

7. The method of claim 1, wherein the oil drilling system further comprises:
   a first communication device coupled to the drill string and configured to communicate with the data acquirer;
   a derrick coupled to the drill string and installed above an earth surface including one or more of land and water;
   a second communication device coupled to the first communication device; and
   a surface computing system coupled to the second communication device at the wellsite.

8. The method of claim 7, further comprising transmitting the last completed page from the memory of the data acquirer to the surface computing system by using the first communication device coupled to the drill string and the second communication device.

9. The method of claim 8, wherein the first communication device is coupled to the second communication device by a cable.

10. The method of claim 8, wherein the first communication device is wirelessly coupled to the second communication device.

11. A data sampling and collection system for oil drilling at a wellsite, the data sampling and collection system comprising: a drill string including a bottom hole assembly comprising a drill bit and a measurement sub; a data acquirer installed in the measurement sub and which includes comprising a controller coupled to a memory and a decoder; a plurality of sampling collectors coupled to the data acquirer and each sampling collector includes a sensor and a plurality of pages of random access memory (RAM) to store sensor data received from the sensor; wherein each of the plurality of sampling collectors collects the sensor data independently and concurrently, and stores the sensor data in the plurality of pages of RAM in each of the plurality of sampling collectors; wherein the plurality of pages of RAM include a current page of RAM currently receiving a plurality of sensor data from the sensor that is vet completely filled and an immediately preceding filled page of RAM storing a last completed page of received plurality of sensor data; wherein the controller transmits a sampling collector identification signal to the decoder, and the decoder transmits an enable signal in response to the sampling collector identification signal, and wherein one of the plurality of sampling collectors receives the enable signal from the decoder so that the decoder selects one of the sampling collectors from the plurality of sampling collectors; wherein the selected sampling collector allows the immediately preceding page of RAM storing the last completed page of the received sensor data of the selected sampling collector to be accessed by the data acquirer and disallows the current page of RAM of the selected sampling collector to be accessed by the data acquirer, and wherein the data acquirer acquires the last completed page of the sensor data from the selected sampling collector and stores the last completed page in the memory of the data acquirer without interrupting the ongoing work of the selected sampling collector filling the current page of RAM with collected sensor data, and without interrupting the ongoing work of a plurality of sampling collectors that are not selected.

12. The data sampling and collection system of claim 11, wherein the memory of the data acquirer stores a predetermined list of sampling collection identification signals.

13. The data sampling and collection system of claim 12, wherein at least one of the sampling collection identification signals appears more than once in the predetermined list.

14. The data sampling and collection system of claim 11, wherein the memory of the data acquirer stores the last completed page of each sampling collector corresponding to the predetermined list of sampling collection identification signals.

15. The data sampling and collection system of claim 11, further comprising a derrick coupled to the drill string and installed above an earth surface including one or more of land and water.

16. The data sampling and collection system of claim 15, further comprising a first communication device coupled to the drill string and configured to communicate with the data acquirer.

17. The data sampling and collection system of claim 16, further comprising a second communication device coupled to the first communication device to receive the last completed page of the plurality of sensor data from the first communication device.

18. The data sampling and collection system of claim 17, further comprising a surface computing system coupled to the second communication device at the wellsite to receive and store the last completed page of the plurality of sensor data.

19. The data sampling and collection system of claim 17, wherein the second communication device is coupled to the first communication device by a cable.

20. The data sampling and collection system of claim 17, wherein the second communication device is wirelessly coupled to the first communication device.

* * * * *